United States Patent [19]

Lewis et al.

[11] 4,186,745
[45] Feb. 5, 1980

[54] POROUS CATHETERS

[76] Inventors: David W. Lewis, Rte. 2, Box 198; James J. Kauzlarich, 1603 Inglewood Dr., both of Charlottesville, Va. 22901

[21] Appl. No.: 877,841

[22] Filed: Feb. 15, 1978

Related U.S. Application Data

[63] Continuation-in-part of Ser. No. 711,067 Jul. 30, 1976, abandoned.

[51] Int. Cl.² .............................................. A61M 25/00
[52] U.S. Cl. .................................. 128/349 R; 128/260
[58] Field of Search .................................. 128/348–351, 128/2 R, 260, 227, 239

[56] References Cited

U.S. PATENT DOCUMENTS

| | | | |
|---|---|---|---|
| 2,863,453 | 12/1958 | Gewecke | 128/239 X |
| 2,912,981 | 11/1959 | Keough | 128/349 B |
| 3,053,257 | 9/1962 | Birtwell | 128/349 B |
| 3,331,371 | 7/1967 | Rocchi | 128/349 B |
| 3,447,161 | 6/1969 | Weikel | 128/348 X |
| 3,593,713 | 7/1971 | Bogoff et al. | 128/349 B |
| 3,640,269 | 2/1972 | Delgado | 128/213 X |
| 3,815,608 | 6/1974 | Spinosa et al. | 128/349 B |
| 3,854,480 | 12/1974 | Zaffaroni | 128/260 |
| 3,965,909 | 6/1976 | Waddell et al. | 128/348 |
| 3,981,299 | 9/1976 | Murray | 128/349 B |

Primary Examiner—Dalton L. Truluck

[57] ABSTRACT

This invention pertains to catheters used with human beings for drainage of any cavity and of a variety of configurations. In particular, the invention is for using a microporous material with interconnected pores of 0.5 to 5 microns diameter such as polyethylene, polypropylene, fluorocarbon or other material that will release a controlled flow or oozing for several days of a liquid from the catheter by differential thermal expansion produced by contact with the patient. The microporous structure of the catheter may be charged with or recharged with liquids such as distilled water, antiseptics, antibiotics, enzymes, etc. which are contained and retained in the interstices so that the catheter may be described as being "self-sterilizing". Also, the catheter has other desirable features including being self-lubricating for ease of insertion and removal, and offering the opportunity for the administration of medication.

5 Claims, 7 Drawing Figures

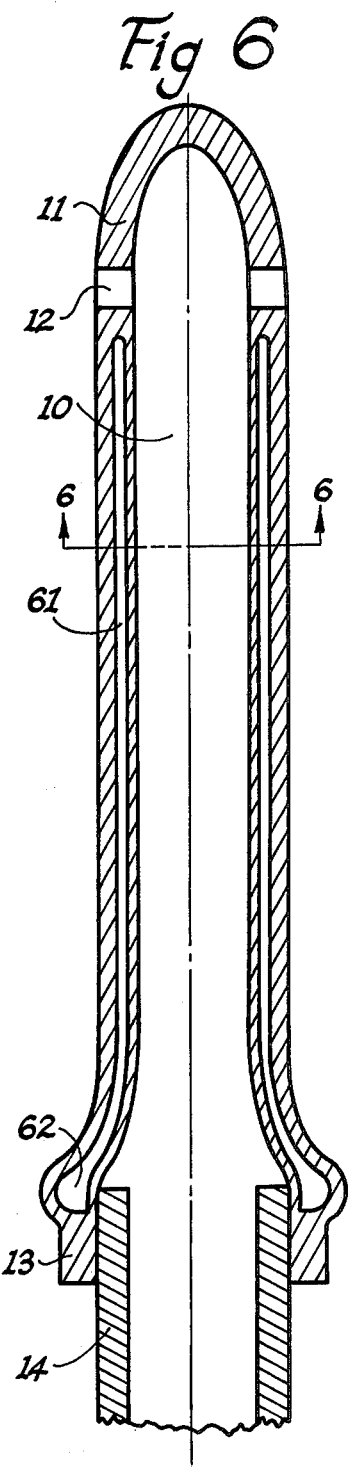
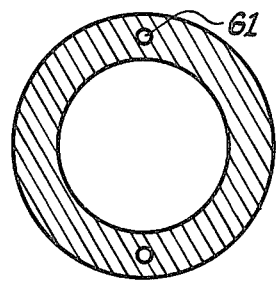
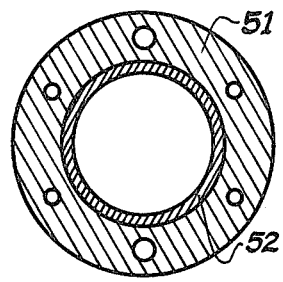
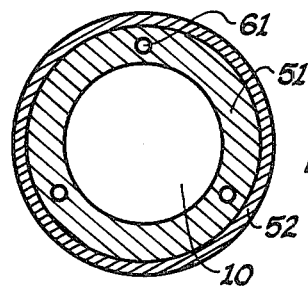
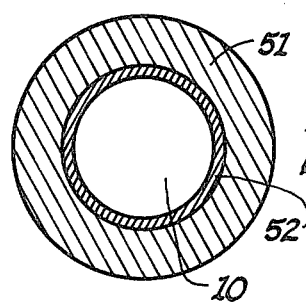

POROUS CATHETERS

CROSS-REFERENCE TO RELATED APPLICATION

This application is a continuation-in-part of patent application U.S. Ser. No. 711,067 filed July 30, 1976, now abandoned.

This invention relates to catheters, and more specifically to improvements in catheters such as are used by physicians and surgeons in hospitals to drain internal organs or wounds or cavities resulting from surgical procedures on patients. More particularly, the invention is concerned with a catheter in which the primary material has a specified or controlled porosity allowing the fluid contained and retained therein to be released from the material at a specified or controlled rate.

The principle object of this invention is to provide an improved catheter characterized by having a micropore structure over a portion of the catheter. The micropore structure will permit a controlled release of substances such as sterile water, antiseptics, antibiotics, enzymes, and other substances which may be contained in the micropore structure as packaged by the manufacturer and/or charged at the time the catheter is to be used, and/or to be charged with one or combinations of the above substances after the catheter has been inserted into the patient.

Another object is to provide a catheter which can be used for the treatment of certain diseases according to the substances applied to and through the micropore structure of the catheter.

Yet another object is to provide a catheter whereby the contact surface between the catheter and patient can be lubricated for easy insertion and/or withdrawal from the patient.

A yet further object comprehends the provision of a catheter whose specified micropore structure can be charged with certain substances, "medications", that will minimize any infections normally associated with the use of catheters.

A still further object comprehends a provision of a catheter which may be "charged " with suitable liquid substances while the catheter is within the patient cavity. This provision will afford the use of medications and also provide the means whereby the catheter can be lubricated in place for easy withdrawal or insertion.

Other objects and important features of this invention will be apparent from a study of the specifications which follow taken in conjunction with the drawings, which together describe and illustrate some preferred embodiments of the invention, and may now be considered the mode of practicing the principles thereof. Other embodiments of the invention may be suggested to those having the benefits of the teaching herein, and such other embodiments are intended to be reserved especially as they fall within the spirit and scope of the subjoined claims.

In the drawings:

FIG. 3 is a transverse cross-sectional view taken along line 1—1 of FIG. 1 showing an alternate charging means through the use of one or more conducting veins in the wall of the catheter;

FIG. 4 is an alternate transverse section of a preferred embodiment that would be visible through section 1—1 of FIG. 1 were the catheter lined with an impervious flexible material;

FIG. 5 is a transverse cross-sectional view taken along the line 3—3 of FIG. 1 looking in the direction of the arrows;

FIG. 6 is a longitudinal cross-sectional view through another preferred embodiment of a catheter of this invention showing a longitudinal loading or charging vein;

FIG. 7 is a transverse cross-sectional view taken along line 1—1 were the catheter lined with an impervious flexible material but with no charging veins.

Figure 1:
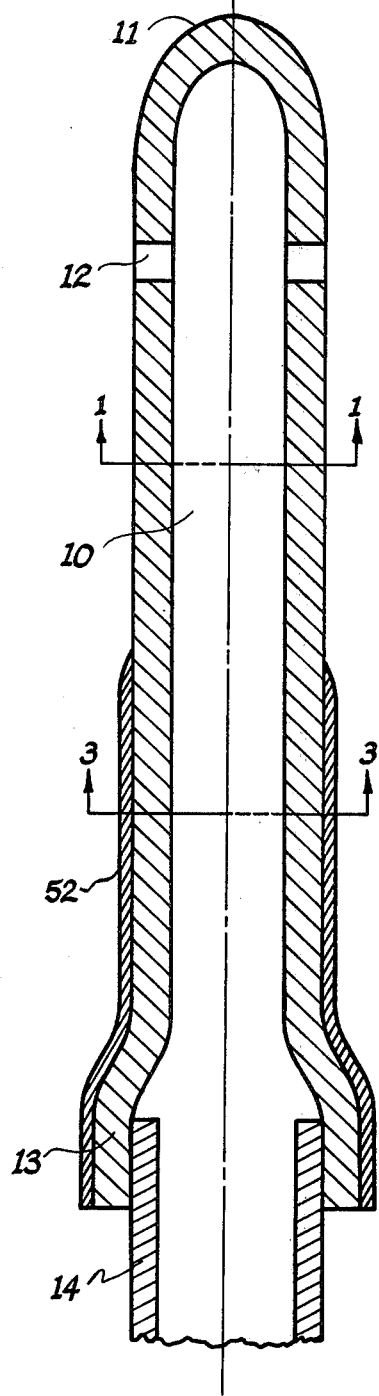
FIG. 1 is a longitudinal cross-sectional view through one embodiment of a catheter improved according to the present invention.

Generally speaking, the catheter illustrated in FIG. 1 for the purpose of exemplifying the invention is a conventional type, it being formed from a flexible although special material and characterized by having a main flow tube 10 which is closed and has a round end at the top as at 11 and is provided with lateral openings 12 and of which the bottom end portion 13 is flared for the connection to an extention tube 14 of a larger diameter. The main material of this catheter will have a pore size, different from the usual rubber material commonly used as catheters, that will be in the range of 0.5 to 5 microns, hereafter referred to as "microporous." The material may be a polyethylene, polypropylene, fluorocarbon, a polyethylene product called Poly-Oil, or other such flexible material whose porosity may be controlled. By suitable choice of the pore size, that is in the size of approximately one micrometer, a catheter of polyethylene suitably loaded or charged with a liquid would "ooze" the liquid for 200 or more hours depending on the viscosity, thermal expansion, temperature exposure of the material, and gravitational force, Jamison et al, "Lubricant Supply Characteristics of a Microporous Polymer", Am. Soc. of Lubrication Eng. Transactions, V 21, No. 1, January, 1978. Oozing will be halted during storage by packaging the catheter within a container flooded with the medicament.

In FIG. 1 the impervious material 13 would act as a seal near the flared end of the catheter.

Figure 2:
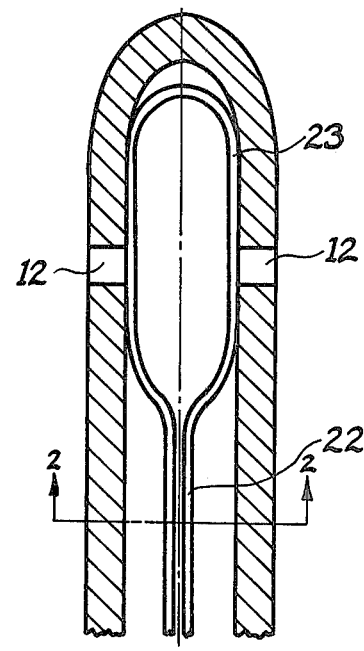
FIG. 2 is a view similar to FIG. 1 but showing the catheter suitably "plugged" at both ends with a charging port noted in the external removable plug.

To facilitate the recharging of the catheter with a desired substance such as sterile water, antiseptics, antibiotics, enzymes, etc., an insertable plug that would be inflated once in position is noted as 22 in FIG. 2 with the inflatable end 23 acting as a plug to the lateral openings 12. The end cap 24 will be suitably designed to permit the insertion of fluid through the opening 25, and also permit the inflation of the plug 23 through the connector tubing 26.

Another preferred embodiment of this invention is noted in FIG. 6 in which the means for recharging the catheter will be through veins or passageways 61 that are integral with the main body 10 with the passageways 61 being interconnected through a circumferential passage 62 that is near the flared end of the catheter 13. Access to the conducting passages 61 through the circumferential passageway 62 may be through a permanent hole into passage 62 or by insertion of a hypodermic needle with syringe into the circumferential passageway 62. The transverse view looking along the line 6—6 of FIG. 6 may appear as FIG. 3 with one, two or more passageways 61. Access to the conducting passages 61 through the circumferential passageway 62 will afford the means for enlarging the passageway 62 thereby providing a pressurized source of liquid for extending the recharging time hence extending the active time for egress or oozing of the liquid through the porous material. The soft material forming passageway 62 will form its own seal upon removal of the hypodermic needle.

A further embodiment of the invention is noted in the transverse section of FIG. 4 showing recharging/charging passageways 61, a porous material 51 and a non-porous material 52. In this embodiment the main flow tube 10 would be essentially isolated from the microporous structure 51, preventing contamination of material conducted through the main channel 10 with the wall of the catheter of the microporous material 51.

In the embodiment of FIG. 5 the impervious or non-porous material 52 serves as a shield preventing any escape or radially outward flow of fluids through the catheter. The combination of non-porous material 52 applied to an external portion of the catheter as in FIG. 5 and to the internal portion of the catheter as in FIG. 7 will yield an embodiment of this invention that will serve uniquely certain applications in the field of medicine.

It is apparent now that the invention may be applied with many ramifications to the many presently used configurations including those catheters with specific means of retention and valved catheters.

One means for producing a microporous catheter charged with certain medicaments is explained in detail in the Jamison et al paper previously cited.

It will be apparent to those skilled in the art that various combinations including substitutions of equivalents may be made in the form of the catheters herein described without departing from the spirit and scope of the invention as set forth in the appended claims, and that in some certain cases features of the invention may be used to advantage without a corresponding use of other features so that numerous details of the construction shown may be altered or omitted without departing from the spirit of the invention as defined by the following claims.

The following claims are herewith declared as new claims.

We claim:

1. A catheter, comprising an annular walled drainage tube with upper and lower ends, having suitable lateral openings at the upper end for receiving body fluids and an outlet at the lower end for discharging such body fluids, said catheter being composed of a flexible material selected from the group of materials consisting of open microporous polyethylene, open microporous polypropylene, open microporous fluorocarbon, open microporous Poly-Oil polyethylene, or other open microporous thermoplastics, of a microporosity in the range of 0.5 to 5 microns, initially containing a liquid medicament and/or lubricant in the interstices of said microporous pores, the size being in the critical range of 0.5 to 5 microns as necessary for the function of flow control of said liquid medicament and/or lubricant so as to retain the liquid medicament and/or lubricant while the catheter is being stored over a long period of time until inserted into a body cavity at which time the liquid will egress or ooze from the catheter due to pressure gradients, and/or gravity gradients, with significant pressure gradients arising from the differential thermal expansion between the microporous catheter material and the liquid medicament and/or lubricant, said differential thermal expansion arising from the change of temperature experienced by the catheter on insertion into a body cavity; said generated liquid medicament and/or lubricant flow from the catheter, being produced by the said differential thermal expansion and persisting for hundreds of hours, thereby providing the functions of self-sterilization, self-lubrication, and self-cleansing.

2. A catheter as claimed in claim 1, providing means for supplying charging liquid or recharging liquid, wherein said liquid is a siloxane, or enzyme, or antiseptic, or sterile water, or antibiotic, while external to the patient or while in place within the patient; said catheter characterized by having one or more vein-like passageways running generally along its length and in its wall; these vein-like passageways being interconnected so that a single access, via a hypodermic needle or simple orifice, will provide the means for charging all of these passageways simultaneously.

3. A catheter as claimed in claim 1, including certain areas that are impervious to liquids as contrasted with the microporosity of the main body; said impervious areas serving to prevent oozing of liquid from the microporous regions at the outlet region of the tube and/or along the interior wall of the catheter thereby limiting oozing of the liquid from the microporous material generally in the radially outward direction, namely toward the contact area of the catheter and patient.

4. A catheter as claimed in claim 1, including a self-lubricating contact surface area, that may be initially charged or recharged with a suitable liquid that will lubricate the contact surface area of the flexible catheter in contact with the patient passageway so as to provide for the easy removal and/or insertion of said catheter.

5. A catheter as claimed in claim 1, including an inflatable circumferential passageway through which the catheter may be recharged with a suitable liquid by a hypodermic needle with a syringe, said passageway made from soft rubber-like material so as to be self-sealing upon removal of the hypodermic needle; said passageway affording a small pressurized reservoir for continuous recharging of the liquid into the porous material of said catheter.

* * * * *